(12) United States Patent
Nair et al.

(10) Patent No.: US 6,875,746 B1
(45) Date of Patent: Apr. 5, 2005

(54) ANTICANCER ANTHRAQUINONES AND METHOD OF USE THEREOF

(75) Inventors: Muraleedharan G. Nair, Okemos, MI (US); Robert H. Cichewicz, Santa Cruz, CA (US); Navindra P. Seeram, Simi Valley, CA (US); Yanjun Zhang, East Lansing, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 144 days.

(21) Appl. No.: 10/355,483

(22) Filed: Jan. 31, 2003

Related U.S. Application Data

(63) Continuation-in-part of application No. 10/317,906, filed on Dec. 12, 2002.
(60) Provisional application No. 60/372,576, filed on Apr. 15, 2002, and provisional application No. 60/389,368, filed on Jun. 17, 2002.

(51) Int. Cl.[7] .................. A01N 43/04; A01N 37/00; A61K 31/70; A61K 31/21
(52) U.S. Cl. .................. 514/33; 514/510; 514/548; 552/208; 552/261; 552/262; 552/265; 552/266; 552/267; 536/18.1; 536/18.2
(58) Field of Search .................. 514/33, 510, 548; 552/208, 261, 262, 265, 266, 267; 536/18.1, 18.2

(56) References Cited

U.S. PATENT DOCUMENTS

| | | | |
|---|---|---|---|
| 5,091,385 A | | 2/1992 | Gulliya et al. |
| 5,177,073 A | | 1/1993 | Gulliya et al. |
| 5,480,873 A | * | 1/1996 | Brunavs et al. |
| 5,489,590 A | | 2/1996 | Gulliya et al. |
| 5,652,265 A | * | 7/1997 | Vittori et al. |
| 5,668,172 A | | 9/1997 | Gallagher et al. |
| 5,733,880 A | * | 3/1998 | Mincher et al. |
| 6,465,522 B1 | | 10/2002 | Potter et al. |

OTHER PUBLICATIONS

Cameron et al., "Synthesis of Specifically O-Alkylated Anthraquinones by Cycloaddition", Tetrahedron Letters, vol. 27, No. 41, pp. 4999–5002, 1986.*
Li et al., "Bioactive Compounds from the Root of Myrsine Africana", Journal of Natural Products, vol. 52, No. 3, pp. 660–662, 1989.*
Juelich et al., "EPR and ENDOR investigations of chrysazin and aclacinomycin A semiquinones", Magnetic Resonance in Chemistry, vol. 29(2), pp. 178–193, 1991.*
McCormick et al., "Biosynthesis of Tetracyclines", Journal of the American Chemical Society, vol. 90(25), pp. 7126–7127, 1968.*
Khan et al., in Synthesis 255–257 (1994).
Cameron et al., in Tetrahedron Letters 27: 4999–5002 (1986).
Baker and Myers, Pharmacol. Res. 8: 763–770 (1991).
Danielsen and Aksnes, Magn. Reson. Chem. 30: 359–360 (1992).
Schripsema et al., Phytochem. 51: 55–60 (1999).
Li and McLaughlin, J. Nat. Prod. 52: 660–662 (1989).
Midiwo and Arot., Int. J. BioChemiPhysics 2: 115–116 (1993).
Brauers et al., J. Nat. Prod. 63: 739–745 (2000).
Li et al., J. Nat. Prod. 63: 653–656 (2000).
Batterham et al., Aust. J. Chem. 14: 637–642 (1961).
Milovanovic et al., J. Serb. Chem. Soc. 61: 423–429 (1996).

* cited by examiner

*Primary Examiner*—James O. Wilson
*Assistant Examiner*—Traviss C. McIntosh, III
(74) *Attorney, Agent, or Firm*—Ian C. McLeod

(57) ABSTRACT

Anthraquinones are described which have anticancer or antitumor activity and which are useful for inhibiting cancer cells and cells comprising tumors in vitro or in vivo. Preferably, the anthraquinones have the chemical formula:

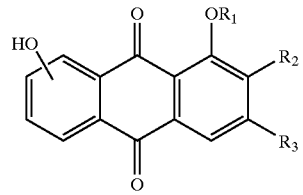

wherein $R_1$ is selected from the group consisting of hydrogen, alkyl, and substituted alkyl; $R_2$ is a group containing 1–12 carbons selected from the group consisting of alkyl, substituted alkyl, aldehyde, hydroxy, hydroxymethyl, acid group, carbohydrate and combinations thereof; and $R_3$ is a group containing 1 to 12 carbons selected from the group consisting of methyl, alkyl, substituted alkyl, aldehyde, hydroxy, hydroxymethyl, acid group, carbohydrate, and combinations thereof. The preferred anthraquinones are 1-hydroxy-2-acetyl-3,6-methyl anthraquinone, 2-acetyl-3,6-methyl anthraquinone monoacetate, 1-hydroxy-2-acetyl-3,7-methyl anthraquinone, 2-acetyl-3,7-methyl anthraquinone monoacetate, 1,2,8-trihydroxy-3-methyl anthraquinone, 1,8-dihydroxy-2-O-β-D-glucopyranoside anthraquinone, 1,2,8-trihydroxy-3-hydroxymethyl anthraquinone, and 1,8-dihydroxy-3-carboxy anthraquinone.

20 Claims, 5 Drawing Sheets

1   $R_1$=H, $R_2$=$CH_3$, $R_3$=H
1a $R_1$=Ac, $R_2$=$CH_3$, $R_3$=H
2   $R_1$=H, $R_2$=H, $R_3$=$CH_3$
2a $R_1$=Ac, $R_2$=H, $R_3$=$CH_3$

3 R=H
4 R=β-D-glucopyranoside

6 R=H

8 R=H

ANTICANCER ANTHRAQUINONES AND METHOD OF USE THEREOF

CROSS-REFERENCE TO RELATED APPLICATION

This application is application is a continuation-in-part of U.S. patent application Ser. No. 10/317,906, filed Dec. 12, 2002, which claims priority to Provisional Application Ser. No. 60/372,576, filed Apr. 15, 2002, and Provisional Application Ser. No. 60/389,368, filed Jun. 17, 2002.

STATEMENT REGARDING FEDERALLY SPONSORED RESEARCH OR DEVELOPMENT

Not applicable.

REFERENCE TO a "COMPUTER LISTING APPENDIX SUBMITTED ON A COMPACT DISC"

Not Applicable.

BACKGROUND OF THE INVENTION (1) Field of the Invention

The present invention relates to anthraquinones which have anticancer or antitumor activity and which are useful for inhibiting growth of cancer cells and tumors in vitro or in vivo. The anthraquinones have the general chemical formula:

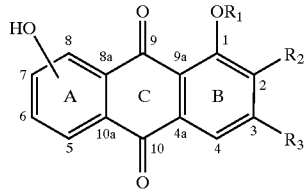

wherein $R_1$ is selected from the group consisting of hydrogen, alkyl, and substituted alkyl; $R_2$ is a group containing 1–12 carbons selected from the group consisting of alkyl, substituted alkyl, aldehyde, hydroxy, hydroxymethyl, acid group, carbohydrate and combinations thereof; and $R_3$ is a group containing 1 to 12 carbons selected from the group consisting of methyl, alkyl, substituted alkyl, aldehyde, hydroxy, hydroxymethyl, acid group, carbohydrate, and combinations thereof in an. The preferred anthraquinones are 1-hydroxy-2-acetyl-3,6-methyl anthraquinone, 2-acetyl-3,6-methyl anthraquinone monoacetate, 1-hydroxy-2-acetyl-3,7-methyl anthraquinone, 2-acetyl-3,7-methyl anthraquinone monoacetate, 1,2,8-trihydroxy-3-methyl anthraquinone, 1,8-dihydroxy-2-O-β-D-glucopyranoside anthraquinone, 1,2,8-trihydroxy-3-hydroxymethyl anthraquinone, and 1,8-dihydroxy-3-carboxy anthraquinone.

(2) Description of Related Art

Many anthraquinone derivatives are potent anticancer or antitumor drugs. The following are examples of U.S. patents which disclose the use of particular anthraquinones as anticancer agents.

U.S. Pat. No. 6,465,522 to Potter et al. discloses of anticancer drugs comprising anthraquinones linked to an alkylating agent.

U.S. Pat. No. 5,733,880 to Mincher discloses particular anthracene derivatives for use as anticancer agents.

U.S. Pat. No. 5,668,172 to Gallagher et al. discloses particular anthraquinones which can be used as anticancer agents.

U.S. Pat. No. 5,652,265 to Vittori et al. discloses the synthesis of the anthraquinone Rhein for use as an antitumor agent.

U.S. Pat. Nos. 5,091,385, 5,177,073, and 5,489,590 to Gulliya et al. disclose a therapeutic mixture comprising a photoactive compound which is capable of killing tumors when activated prior to use with an activating agent such as a chemical, radiation (preferably, irradiation with a laser), gamma rays, or electrons from an electropotential device. The photoactive compounds include a general suggestion of anthraquinones.

In light of the above, there remains a need for novel compounds with anticancer or antitumor activity to increase the arsenal of drugs for combating cancers in warm-blooded animals, including humans.

SUMMARY OF THE INVENTION

The present invention provides a method for inhibiting the growth of cancer cells or tumors in vivo or in vitro by exposing the cancer cells to an inhibitory amount of one or more anthraquinones. The present invention is particularly useful as an agent for inhibiting cancer cells such as those cells comprising breast cancer, lung cancer, central nervous system cancer, or colorectal cancer in vivo or in vitro. The anthraquinones can be substituted with halogens such as I, F, Br, and Cl in the ring, particularly where hydroxyl groups are not located. The substituents in the ring can also include one or more of the halogens. The anthraquinones have the general formula:

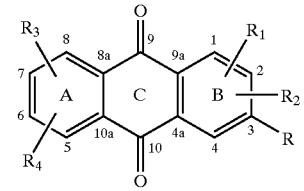

wherein $R_1$, $R_2$, $R_3$, and $R_4$ are each selected from the group consisting of hydrogen, hydroxy, halogen, alkyl, substituted alkyl, alkene, substituted alkene, alkyne, aryl, substituted aryl, cyclic, substituted cyclic, acid group, carbohydrate, and combinations thereof, R is a group containing 1 to 12 carbons selected from the group consisting of methyl, alkyl, substituted alkyl, aldehyde, hydroxy, hydroxymethyl, acid group, carbohydrate, and combinations thereof, and the halogen is selected from the group consisting of I, F, Br, and Cl.

Preferably, the anthraquinones have the general chemical formula:

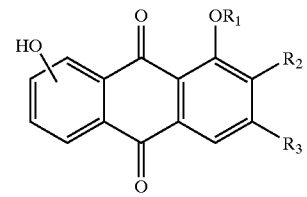

wherein $R_1$ is selected from the group consisting of hydrogen, alkyl, and substituted alkyl; $R_2$ is a group containing 1–12 carbons selected from the group consisting of alkyl, substituted alkyl, aldehyde, hydroxy, hydroxymethyl, acid group, carbohydrate and combinations thereof; and $R_3$ is a group containing 1 to 12 carbons selected from the group consisting of methyl, alkyl, substituted alkyl, aldehyde, hydroxy, hydroxymethyl, acid group, carbohydrate, and combinations thereof.

As used herein, the term "inhibitory" means either to substantially limit the growth of the cells comprising a cancer or tumor, to stop the growth of a substantial number of the cells comprising a cancer or tumor, or to kill a substantial number of the cells comprising a cancer or a tumor. The inhibitory effect includes the ability to induce a substantial number of the cells comprising a cancer or tumor to undergo differentiation and further includes the ability to arrest the growth of a tumor or to cause regression of the tumor. Thus, the term embraces any affect which adversely affects the growth and replication of cancer cells or tumors.

Therefore, the present invention provides a method for inhibiting cells of a cancer or a tumor, which comprises exposing the cells to one or more anthraquinones with the chemical formula:

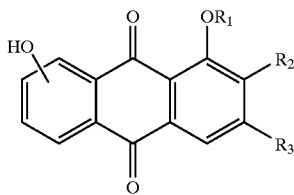

wherein $R_1$ is selected from the group consisting of hydrogen, alkyl, and substituted alkyl; $R_2$ is a group containing 1–12 carbons selected from the group consisting of alkyl, substituted alkyl, aldehyde, hydroxy, hydroxymethyl, acid group, carbohydrate and combinations thereof; and $R_3$ is a group containing 1 to 12 carbons selected from the group consisting of methyl, alkyl, substituted alkyl, aldehyde, hydroxy, hydroxymethyl, acid group, carbohydrate, and combinations thereof, but not an anthroquinone wherein $R_1$ is hydrogen, $R_2$ is hydroxyl, and $R_3$ is methyl, in an amount sufficient to substantially inhibit the cells.

Preferably, the anthraquinones are selected from the group consisting of 1-hydroxy-2-acetyl-3,6-methyl anthraquinone, 2-acetyl-3,6-methyl anthraquinone monoacetate, 1-hydroxy-2-acetyl-3,7-methyl anthraquinone, 2-acetyl-3,7-methyl anthraquinone monoacetate, 1,8-dihydroxy-2-O-β-D-glucopyranoside anthraquinone, and 1,2,8-trihydroxy-3-hydroxymethyl anthraquinone, in an amount sufficient to substantially inhibit the cells.

In a further embodiment of the method, the method further includes providing at least one compound selected from the group consisting of 1,2,8-trihydroxy-3-methyl anthraquinone, 1,8-dihydroxy-3-carboxy anthraquinone, and adriamycin.

In a further embodiment of the method, the cells are selected from the group consisting of breast cancer, central nervous system cancer, lung cancer, and colorectal cancer.

In a further embodiment of the method, the inhibiting is either in vivo or in vitro.

In a further embodiment of the method, the anthraquinone is at a dosage of about 0.1 to 4,000 micrograms per milliliter or gram.

The present invention further provides a method for inhibiting a cancer or tumor in a patient with the cancer or tumor comprising (a) providing a composition containing an inhibitory amount of one or more anthraquinones with the chemical formula:

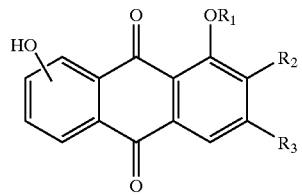

wherein $R_1$ is selected from the group consisting of hydrogen, alkyl, and substituted alkyl; $R_2$ is a group containing 1–12 carbons selected from the group consisting of alkyl, substituted alkyl, aldehyde, hydroxy, hydroxymethyl, acid group, carbohydrate and combinations thereof; and $R_3$ is a group containing 1 to 12 carbons selected from the group consisting of methyl, alkyl, substituted alkyl, aldehyde, hydroxy, hydroxymethyl, acid group, carbohydrate, and combinations thereof, but not an anthroquinone wherein $R_1$ is hydrogen, $R_2$ is hydroxyl, and $R_3$ is methyl, in a pharmaceutically acceptable carrier; and (b) and administering the composition to the patient in an amount sufficient to substantially inhibit the cancer or tumor.

Preferably, the anthraquinones are selected from the group consisting of 1-hydroxy-2-acetyl-3,6-methyl anthraquinone, 2-acetyl-3,6-methyl anthraquinone monoacetate, 1-hydroxy-2-acetyl-3,7-methyl anthraquinone, 2-acetyl-3,7-methyl anthraquinone monoacetate, 1,8-dihydroxy-2-O-β-D-glucopyranoside anthraquinone, and 1,2,8-trihydroxy-3-hydroxymethyl anthraquinone.

In a further embodiment of the method, the composition further includes at least one compound selected from the group consisting of 1,2,8-trihydroxy-3-methyl anthraquinone, 1,8-dihydroxy-3-carboxy anthraquinone, and adriamycin.

In a further embodiment of the method, the cancer or tumor is selected from the group consisting of breast cancer, central nervous system cancer, lung cancer, and colorectal cancer.

In a further embodiment of the method, the anthraquinone is at a dosage of about 0.1 to 4,000 micrograms per milliliter or gram.

In a further embodiment of the method, the composition is administered to the patient by a method selected from the group consisting of oral, subcutaneous, intraperitoneal, topical, intranasal, intravenous, or rectal.

The present invention further provides a composition for inhibiting cells of a cancer or a tumor which comprises (a) one or more anthraquinones with the chemical formula:

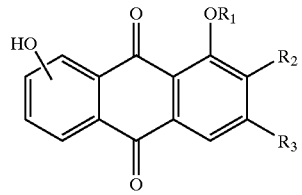

wherein $R_1$ is selected from the group consisting of hydrogen, alkyl, and substituted alkyl; $R_2$ is a group containing 1–12 carbons selected from the group consisting of alkyl, substituted alkyl, aldehyde, hydroxy, hydroxymethyl, acid group, carbohydrate and combinations thereof; and $R_3$ is a group containing 1 to 12 carbons selected from the group consisting of methyl, alkyl, substituted alkyl, aldehyde, hydroxy, hydroxymethyl, acid group, carbohydrate, and combinations thereof but not an anthroquinone wherein $R_1$ is hydrogen, $R_2$ is hydroxyl, and $R_3$ is methyl; and (b) a pharmaceutically acceptable carrier, wherein the composition contains between about 0.1 and 4,000 micrograms of the anthraquinone per milliliter or gram of the carrier.

Preferably, the anthraquinones are selected from the group consisting of 1-hydroxy-2-acetyl-3,6-methyl anthraquinone, 2-acetyl-3,6-methyl anthraquinone monoacetate, 1-hydroxy-2-acetyl-3,7-methyl anthraquinone, 2-acetyl-3,7-methyl anthraquinone monoacetate, 1,8-dihydroxy-2-O-β-D-glucopyranoside anthraquinone, and 1,2,8-trihydroxy-3-hydroxymethyl anthraquinone.

In a further embodiment of the composition, the composition further includes at least one compound selected from the group consisting of 1,2,8-trihydroxy-3-methyl anthraquinone, 1,8-dihydroxy-3-carboxy anthraquinone, and adriamycin.

The present invention further provides an anthraquinone which has the formula:

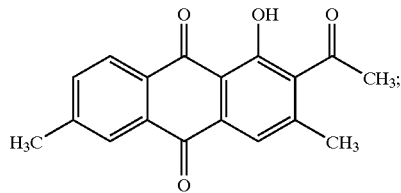

an isolated and purified anthraquinone which has the an anthraquinone which has the formula:

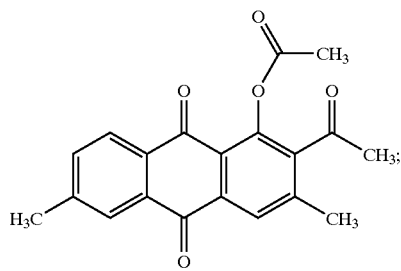

an anthraquinone which has the formula:

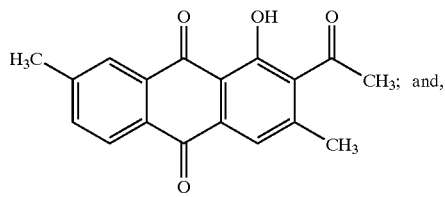

an anthraquinone which has the formula:

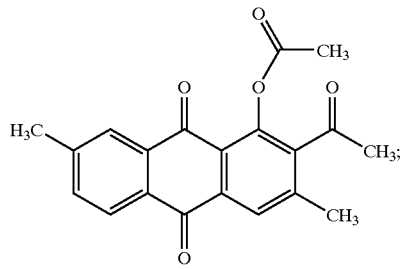

Thus, the present invention provides anthraquinones which have the formula:

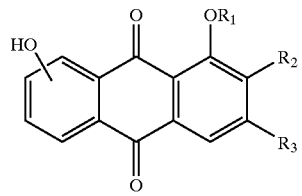

wherein $R_1$ is selected from the group consisting of hydrogen, alkyl, and substituted alkyl; $R_2$ is a group containing 1–12 carbons selected from the group consisting of alkyl, substituted alkyl, aldehyde, hydroxy, hydroxymethyl, acid group, carbohydrate and combinations thereof; and $R_3$ is a group containing 1 to 12 carbons selected from the group consisting of methyl, alkyl, substituted alkyl, aldehyde, hydroxy, hydroxymethyl, acid group, carbohydrate, and combinations thereof but not an anthroquinone wherein $R_1$ is hydrogen, $R_2$ is hydroxyl, and $R_3$ is methyl.

OBJECTS

Therefore, it is an object of the present invention to provide compositions such as the anthraquinones disclosed herein which have anticancer or antitumor activity.

It is further an object of the present invention to provide methods for using the anthraquinones to inhibit the growth of cancer cells or tumors in warm-blooded animals, including humans.

Further still, it is an object of the present invention to provide compositions such as the anthraquinones disclosed herein for chemotherapeutic treatments for cancer.

These and other objects of the present invention will become increasingly apparent with reference to the following drawings and preferred embodiments.

DETAILED DESCRIPTION OF THE INVENTION

All patents, patent applications, government publications, government regulations, and literature references cited in this specification are hereby incorporated herein by reference in their entirety. In case of conflict, the present description, including definitions, will control.

The anthraquinones of the present invention have the ability to inhibit the growth of cells comprising a cancer or a tumor. Therefore, the present invention provides anthraquinones and methods for their use as anticancer or antitumor agents for chemotherapeutic treatments of warm-blooded animals, including humans. In particular, the anthraquinones are hydroxy-substituted anthraquinones which are useful per se for the anticancer or antitumor applications or as components in other anticancer or antitumor compositions. Hydroxy-substituted anthraquinones can be derived synthetically as described by Khan et al., in Synthesis 255–257 (1994) and by Cameron et al. in Tetrahedron Letters 27: 4999–5002 (1986) or can be isolated from plant sources such as the roots of daylilies (*Hemerocallis fulva*) as described hereinafter.

The anthraquinones of the present invention provide a means for treating many cancers or tumors which is non-invasive and which has less severe side-effects than many of the current anticancer and antitumor therapies such as radiation therapy and chemotherapy. For particularly recalcitrant cancers or tumors, the anthraquinones of the present invention can be used in conjunction with other anticancer or antitumor treatments such as radiation and chemotherapies and invasive methods such as surgical removal of cancerous tissue or tumors.

Figure 1:
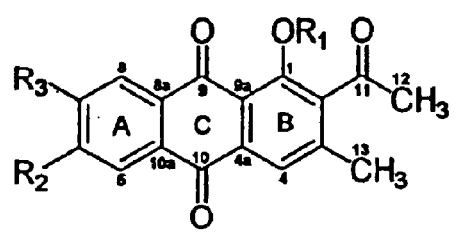
FIG. 1 is a chart showing the chemical structure of compounds 1, 1a, 2, 2a, 3, 4, 6, and 8 isolated from daylily roots of *Hemerocallis fulva* "Kwanzo" Kaempfer. Ac refers to acetyl groups such as —COCH$_3$.
Figure 1:
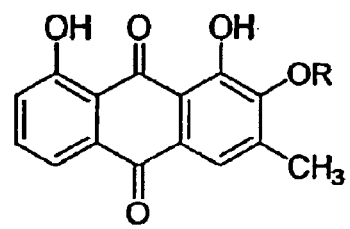
Figure 1:
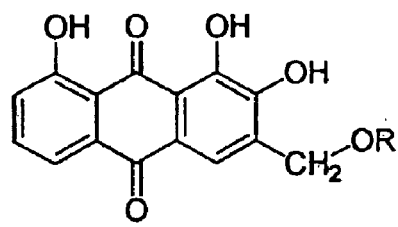
Figure 1:
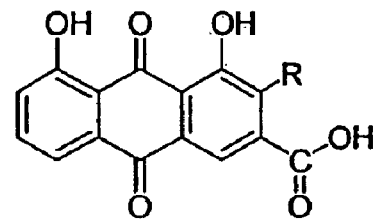

As described more fully in the Examples, the roots of *H. fulva* (Kwanzo) were extracted with hexane, EtOAc, and MeOH. The hexane and MeOH extracts were selected for further study and subsequently subjected to a combination of chromatographic procedures including Si gel MPLC and PTLC, ODS MPLC and preparative HPLC, and crystallization. This led to the discovery and isolation of nine novel anthraquinones, the kwanzoquinones: kwanzoquinone A (compound 1: (1-hydroxy-2-acetyl-3,6-methyl anthraquinone); kwanzoquinone A monoacetate (compound 1a: (2-acetyl-3,6-methyl anthraquinone monoacetate); kwanzoquinone B (compound 2: (1-hydroxy-2-acetyl-3,7-methyl anthraquinone); kwanzoquinone B monoacetate (compound 2a: (2-acetyl-3,7-methyl anthraquinone monoacetate); kwanzoquinone C (compound 4: (1,8-dihydroxy-2-O-β-D-glucopyranoside anthraquinone); and, kwanzoquinone E (compound 6: (1,2,8-trihydroxy-3-hydroxymethyl anthraquinone). The structures and complete $^1$H and $^{13}$C NMR spectral assignments for anthraquinones 3 (1,2,8-hydroxy-3-methylanthraquinone or 2-hydroxychrysophanol) and 8 (1,8-dihydroxy-3-carboxy anthraquinone or rhein) were made based on thorough 1D and 2D NMR. The structures of the above compounds are shown in FIG. 1. The anthraquinones are soluble in a variety of protic and aprotic solvents including, but not limited to, DMSO, alcohols such as ethanol, aqueous alkali hydroxide solutions, $Na_2CO_3$ solutions, and $NH_3$ solutions.

The anthraquinones described herein were discovered to be able to substantially inhibit the growth of cancer cells. This indicates that the anthraquinones herein are useful for cancer treatments and therapies when provided to a patient either individually or in various combinations with each other or with other compounds which have anticancer or antitumor activity. In particular, as shown in the Examples, anthraquinones 1, 1a, 2, 2a, 3, 4, 6, and 8 have been discovered to have the ability to inhibit the growth of cells derived from a human breast carcinoma (cell line MCF-7), a human central nervous system carcinoma (cell line SF-268), a human lung carcinoma (cell line NCI-H460), and a human colorectal carcinoma (cell line HCT-116; ATCC CCL-247). Table 5 shows that the amount of each of the anthraquinones which would provide 50% growth inhibition ($GI_{50}$) against particular cancer cells ranged from between about 1.8 and 21.1 µg/mL. In light of the ability of the anthraquinones to inhibit various types of cancer cells, the anthraquinones are useful as antitumor or antiproliferative agents for cancer chemotherapeutic applications, particularly, for therapies for human breast cancers, human lung cancers, human central nervous system cancers, and human colorectal cancers.

The anthraquinones which have anticancer or antitumor activity and, therefore, are useful as anticancer or antitumor agents have the following general chemical formula:

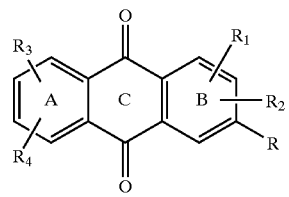

wherein $R_1$, $R_2$, $R_3$, and $R_4$ are each selected from the group consisting of hydrogen, hydroxy, halogen, alkyl, substituted alkyl, alkene, substituted alkene, alkyne, aryl, substituted aryl, cyclic, substituted cyclic, acid group, carbohydrate, and combinations thereof, R is a group containing 1 to 12 carbons selected from the group consisting of methyl, alkyl, substituted alkyl, aldehyde, hydroxy, hydroxymethyl, acid group, carbohydrate, and combinations thereof, and the halogen is selected from the group consisting of I, F, Br, and Cl.

In preferred embodiments, the anthraquinones have the following general chemical formula:

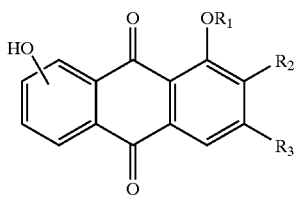

wherein R₁ is selected from the group consisting of hydrogen, alkyl, and substituted alkyl; R₂ is a group containing 1–12 carbons selected from the group consisting of alkyl, substituted alkyl, aldehyde, hydroxy, hydroxymethyl, acid group, carbohydrate and combinations thereof; and R₃ is a group containing 1 to 12 carbons selected from the group consisting of methyl, alkyl, substituted alkyl, aldehyde, hydroxy, hydroxymethyl, acid group, carbohydrate, and combinations thereof.

The preferred anthraquinones with anticancer or antitumor activity with the above general chemical formula are 1-hydroxy-2-acetyl-3,6-methyl anthraquinone, which is compound 1 isolated from daylilies and which has the trivial name kwanzoquinone A, and which has the chemical formula:

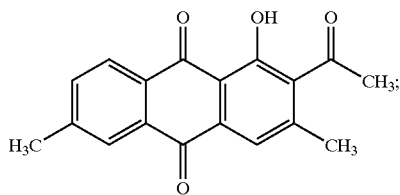

1-hydroxy-2-acetyl-3,6-methyl anthraquinone monoacetate, which is compound 1a isolated from daylilies and which has the trivial name kwanzoquinone A monoacetate, and which has the chemical formula:

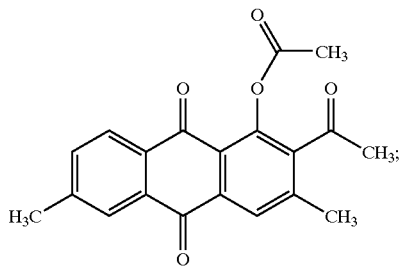

1-hydroxy-2-acetyl-3,7-methyl anthraquinone, which is compound 2 isolated from daylilies and which has the trivial name kwanzoquinone B, and which has the chemical formula:

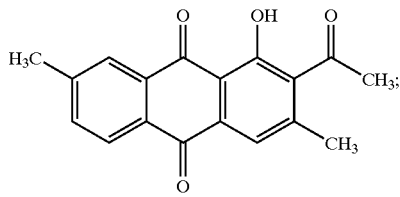

1-hydroxy-2-acetyl-3,7-methyl anthraquinone monoacetate, which is compound 2a isolated from daylilies and which has the trivial name kwanzoquinone B monoacetate, and which has the chemical formula:

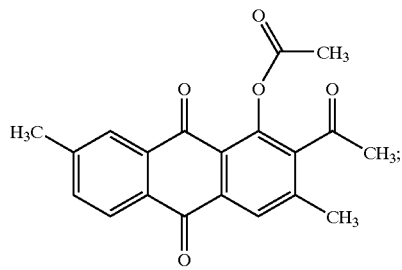

1,2,8-trihydroxy-3-methyl anthraquinone, which is compound 3 isolated from daylilies and which has the trivial name 2-hydroxychrysophanol, and which has the chemical formula:

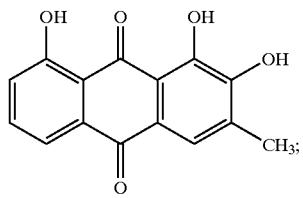

1,8-dihydroxy-2-O-β-glucopyranoside-3-methyl anthraquinone, which is novel compound 4 isolated from daylilies and which has been given the trivial name kwanzoquinone D, and which has the chemical formula:

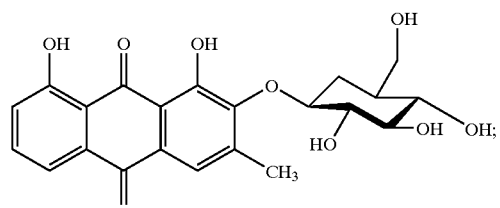

1,2,8-trihydroxy-3-hydroxymethyl anthraquinone, which is novel compound 6 isolated from daylilies and which has been given the trivial name kwanzoquinone E, and which has the chemical formula:

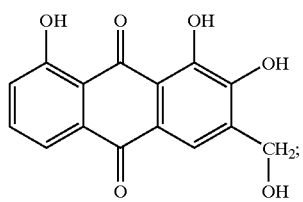

and 1,8-dihydroxy-3-carboxy anthraquinone, which is compound 8 isolated from daylilies and which has the trivial name rhein, and which has the chemical formula:

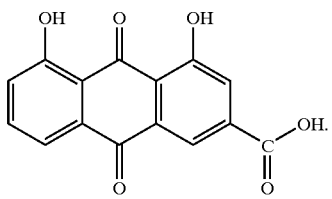

The method for inhibiting the cells of a cancer or tumor in a patient (warm-blooded animal or human) with the cancer or tumor, comprises providing to the animal a composition comprising as the active ingredient an inhibitory amount of one or more of anthraquinones with the general chemical formulae shown above. Preferably, the one or more anthraquinones are selected from the group consisting of 1, 1a, 2, 2a, 3, 4, 6, and 8. In a further embodiment, the compositions can further include adriamycin or mitoxantrone, or both. In the aforementioned compositions, the anthraquinone is inhibitory at a dosage of 0.1 to 4,000 micrograms per milliliter or gram.

In the case of isolating compounds 1, 1a, 2, and 2a, from daylilies, compound 1 is not readily separable from compound 2 and compound 1a is not readily separable compound 2a. Instead, compounds 1 and 2 are more readily isolated as a mixture of 1 and 2 and compounds 1a and 2a are more readily isolated as a mixture of 1a and 2a. Because of the difficulty in separating 1 from 2 or 1a from 2a, it is more convenient to provide compositions for treating a patient with a cancer or tumor which comprise a mixture of 1 and 2 or a mixture of 1a and 2a or a mixture containing all four. The mixtures can be further combined with one or more of the other compounds disclosed herein.

In a preferred embodiment, one or more of the anthraquinones for treating a patient with a cancer or tumor are provided to the patient at an inhibitory dose, which is at an amount which does not kill normal cells in the patient, in a pharmaceutically acceptable carrier. Preferably, the inhibitory dose is the 50% growth inhibitory ($GI_{50}$) value for the anthraquinones for the particular cancer or tumor afflicting the patient. As such, the anthraquinones are processed with pharmaceutical carrier substances by methods well known in the art such as by means of conventional mixing, granulating, coating, suspending and encapsulating methods, into the customary preparations for oral or rectal administration. Thus, anticancer or antitumor anthraquinone preparations for oral application can be obtained by combining one or more of the anthraquinones with solid pharmaceutical carriers; optionally granulating the resulting mixture; and processing the mixture or granulate, if desired and/or optionally after the addition of suitable auxiliaries, into the form of tablets or dragee cores.

Suitable pharmaceutical carriers for solid preparations are, in particular, fillers such as sugar, for example, lactose, saccharose, mannitol or sorbitol, cellulose preparations and/or calcium phosphates, for example, tricalcium phosphate or calcium hydrogen phosphate; also binding agents, such as starch paste, with the use, for example, of maize, wheat, rice or potato starch, gelatine, tragacanth, methyl cellulose, hydroxypropylmethyl cellulose, sodium carboxymethyl cellulose and/or polyvinylpyrrolidone, esters of polyacrylates or polymethacrylates with partially free functional groups; and/or, if required, effervescent agents, such as the abovementioned starches, also carboxymethyl starch, cross-linked polyvinylpyrrolidone, agar, or alginic acid or a salt thereof, such as sodium alginate. Auxiliaries are primarily flow-regulating agents and lubricating agents, for example, silicic acid, talcum, stearic acid or salts thereof, such as magnesium stearate or calcium stearate. Dragee cores are provided with suitable coatings, optionally resistant to gastric juices, whereby there are used, inter alia, concentrated sugar solutions optionally containing gum arabic, talcum, polyvinylpyrrolidone, and/or titanium dioxide, lacquer solutions in aqueous solvents or, for producing coatings resistant to is stomach juices, solutions of esters of polyacrylates or polymethacrylates having partially free functional groups, or of suitable cellulose preparations such as acetylcellulose phthalate or hydroxypropylmethylcellulose phthalate, with or without suitable softeners such as phthalic acid ester or triacetin. Dyestuffs or pigments may be added to the tablets or dragee coatings, for example for identification or marking of the various doses of active ingredient.

Anticancer or antitumor preparations comprising one or more of the anthraquinones which can be administered orally further include hard gelatine capsules, as well as hard or soft closed capsules made from gelatine and, if required, a softener such as glycerin or sorbitol. The hard gelatine capsules can contain one or more of the anthraquinones in the form of a granulate, for example in admixture with fillers such as maize starch, optionally granulated wheat starch, binders or lubricants such as talc magnesium stearate or colloidal silicic acid, and optionally stabilizers. In closed capsules, the one or more of the anthraquinones is in the form of a powder or granulate; or it is preferably present in the form of a suspension in suitable solvent, whereby for stabilizing the suspensions there can be added, for example, glycerin monostearate.

Other anticancer or antitumor preparations to be administered orally are, for example, aqueous suspensions prepared in the usual manner, which suspensions contain the one or more of the anthraquinones in the suspended form and at a concentration rendering a single dose sufficient. The aqueous suspensions either contain at most small amounts of stabilizers and/or flavoring substances, for example, sweetening agents such as saccharin-sodium, or as syrups contain a certain amount of sugar and/or sorbitol or similar substances. Also suitable are, for example, concentrates or concentrated suspensions for the preparation of shakes. Such concentrates can also be packed in single-dose amounts.

Suitable anticancer or antitumor preparations for rectal administration are, for example, suppositories consisting of a mixture of one or more of the anthraquinones with a suppository foundation substance. Such substances are, in particular, natural or synthetic triglyceride mixtures. Also suitable are gelatine rectal capsules consisting of a suspension of the one or more of the nthraquinones in a foundation substance. Suitable foundation substances are, for example, liquid triglycerides, of higher or, in particular, medium saturated fatty acids.

Likewise of particular interest are preparations containing the finely ground one or more of the anthraquinones, preferably that having a median of particle size of 5 µm or less, in admixture with a starch, especially with maize starch or wheat starch, also, for example, with potato starch or rice starch. They are produced preferably by means of a brief mixing in a high-speed mixer having a propeller-like, sharp-edged stirring device, for example with a mixing time of between 3 and 10 minutes, and in the case of larger amounts of constituents with cooling if necessary. In this mixing process, the particles of the one or more of the anthraquinones are uniformly deposited, with a continuing reduction of the size of some particles, onto the starch particles. The mixtures mentioned can be processed with the customary, for example, the aforementioned, auxiliaries into the form of solid dosage units; i.e., pressed for example into the form of tablets or dragees or filled into capsules. They can however also be used directly, or after the addition of auxiliaries, for example, pharmaceutically acceptable wetting agents and distributing agents, such as esters of polyoxyethylene sorbitans with higher fatty acids or sodium lauryl sulphate, and/or flavoring substances, as concentrates for the preparation of aqueous suspensions, for example, with about 5- to 20-fold amount of water. Instead of combining the anthraquinone/starch mixture with a surface-active substance or with other auxiliaries, these substances may also be added to the water used to prepare the suspension. The concentrates for producing suspensions, consisting of the one or more of the anthraquinones/starch mixtures and optionally auxiliaries, can be packed in single-dose amounts, if required in an airtight and moisture-proof manner.

In addition, the one or more anthraquinones can be administered to a patient intraperitoneally, intranasally, subcutaneously, or intravenously. In general, for intraperitoneal, intranasal, subcutaneous, or intravenous administration, one or more of the above compositions or anthraquinones are provided by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives. Preferably, the one or more anthraquinones are provided in a composition acceptable for intraperitoneal, subcutaneous, or intravenous use in warm-blooded animals or humans. For example, such compositions can comprise a physiologically acceptable solution such as a buffered phosphate salt solution as a carrier for the one or more anthraquinones. Preferably, the solution is at a physiological pH. In particular embodiments, the composition is injected directly into the tumor or perfused through the tumor by intravenous administration.

Anticancer or antitumor preparations according to the present invention comprise one or more of the anthraquinones at a concentration suitable for administration to warm-blooded animals or humans which concentration is, depending on the mode of administration, between about 0.3% and 95%, preferably between about 2.5% and 90%. In the case of suspensions, the concentration is usually not higher than 30%, preferably about 2.5%; and conversely in the case of tablets, dragees and capsules with the one or more of the anthraquinones, the concentration is preferably not lower than about 0.3%, in order to ensure an easy ingestion of the required doses of the one or more anthraquinones. The treatment of cancers and tumors in patients with the preparations comprising one or more of the anthraquinones is carried out preferably by one or more administrations of a dose of the one or more anthraquinones which over time is sufficient to substantially inhibit the cancer or tumor, that is to say, an amount which is sufficient to cause complete or partial remission of the cancer or tumor. If required, the doses can be administered daily or divided into several partial doses which are administered at intervals of several hours. In particular cases, the preparations can be used in conjunction with or following one or more other anticancer or antitumor therapies such as radiation or chemotherapy, or in conjunction with surgical procedures for removing cancers or tumors. The administered dose of the one or more anthraquinones, is dependent both on the patient (species of warm-blooded animal or human) to be treated, the general condition of the patient to be treated, and on the type of cancer or tumor to be treated.

The following examples are intended to promote a further understanding of the present invention.

EXAMPLE 1

This example illustrates the extraction and isolation of the kwanzoquinones from daylilies.

*Hemoricallis fulva* (Kwanzo) plants were purchased from the Perennial Patch (Wade, N.C.) in August 1999. The plants were grown on the Michigan State University Campus before being harvested in April 2001. The leaves were removed and the roots and crowns of 124 plants were washed and frozen at −4° C. The frozen roots were lyophilized and ground in a WARING blender yielding 2.2 kg of fine light-brown powder.

For isolation and purification of 1, 1a, 2, 2a, 3, 4, 6, and 8 involved the use of SEPHADEX LH-20 (Sigma-Aldrich, St. Louis, Mo.), Si gel (particle size 40–63 $\mu$m) from Fischer Scientific (Pittsburgh, Pa.), AMBERLITE XAD-16 resin from Supelco (Bellafonte, Pa.), LC-SORB SP-A-ODS gel (particle size 25–40 $\mu$m) from Dychrom (Santa Clara, Calif.), and Si gel PTLC plates (20×20 cm; 250, 500, and 1000 $\mu$m thick) from Analtech, Inc. (Newark, Del.). Preparative HPLC was performed on a Japan Analytical Industry Co. model LC-20 recycling preparative HPLC with a JAIGEL-$C_{18}$ column (10 $\mu$m, 20 mm×250 mm). All solvents and chemicals were purchased from Spectrum Laboratory Products, Inc. (New Brunswick, N.J.) and were of ACS analytical grade.

The lyophilized roots (2.0 kg) were sequentially extracted with 3×8 L portions of hexane ethyl acetate, and methanol yielding 25, 23, and 130 g of extract, respectively. The hexane extract was redissolved in 500 mL of hexane and partitioned with 3×500 mL portions of methanol. The methanol fractions were pooled yielding 15 g of extract which was applied to Si gel VLC and eluted with 4 L hexane, 3 L hexane-acetone (9:1), and 3 L hexane-acetone (3:2). The hexane elute (8.5 g) was subjected to Si gel MPLC under gradient conditions with 100% hexane to 100% acetone and 200 mL fractions were collected. All fractions were analyzed by TLC and pooled according to similarities in their profiles yielding fractions A1 to A4.

The hexane-acetone (9:1) eluate from the Si gel VLC was subjected to Si gel MPLC under gradient conditions with 100% hexane to hexane-acetone (1:1) providing fractions B1 to B4.

Fraction B2 (1.5 g) was rechromatographed by Si gel MPLC under gradient conditions with 100% hexane to 100% EtOAc and 200 mL fractions were collected and pooled based on TLC profiles giving fractions C1 to C4.

Fractions A3 (1 g), A4 (1 g), C2 (300 mg), and C3 (300 mg) were pooled based further examination by TLC and applied to Si gel MPLC. Elution was carried out under gradient conditions with 100% hexane to 100% $CHCl_3$ to $CHCl_3$-ethanol (1:1) 18 mL fractions D1 to D90 were collected.

Fractions D1 to D10 were pooled (500 mg) and further subjected to Si gel MPLC under gradient conditions with 100% hexane to hexane-acetone (97:3) and 15 mL fractions E1 to E40 were collected.

Fractions E6 to E20 (200 mg) were composed of primarily one major component and thus pooled and subjected to sequential Si gel PTLC with hexane-EtOAc (10:1) (72 mg), hexane-diethyl ether (6:1) (51 mg), and benzene-$CHCl_3$ (20:1) yielding 30 mg of α-tocopherol as a clear oil that exhibited spectral characteristics identical to those reported in the literature (Baker and Myers, Pharmacol. Res. 8: 763–770 (1991)).

Fractions D12 to D45 (300 mg) were combined, applied to Si gel PTLC plates, and developed in benzene-$CHCl_3$ (10:1) twice. A bright yellow band (44 mg) was obtained and following extraction from the Si gel, it was dissolved in a minimal volume of $CHCl_3$ and hexane added drop-wise until a slight degree of turbidity was noted. The solution was stored at −20° C. yielding an inseparable 1:1 mixture (based on $^1H$ NMR) of compounds 1 and 2 as fine yellow needles (12 mg). Both compounds 1 and 2 and their mono acetates 1a and 2a (prepared from $Ac_2O$/pyridine) were subjected to a variety of chromatographic techniques including further Si gel TLC and MPLC, as well as, ODS MPLC and ODS preparative HPLC, but failed to separate these two compounds.

The MeOH extract of the roots was dissolved in 800 mL MeOH—$H_2O$ (3:1) and left at 4° C. until a precipitate formed. The mixture was centrifuged (16,000×g, 15 min, 4° C.) and the supernatant decanted to give 30 g of extract. This was applied to a column of XAD-16 resin and eluted with 10 L $H_2O$, 6 L 25% aqueous MeOH, and 8 L 100% MeOH. The MeOH eluate (18 g) was dissolved in 500 mL $H_2O$ and partitioned with $CHCl_3$ (3×300 mL). The $CHCl_3$ fractions were pooled and dried yielding 2 g of extract that was applied to ODS MPLC and eluted with 50 to 100% MeOH and 16 mL fractions F1 to F166 were collected. Fractions F116 to F125 were pooled giving 100 mg of residue that was dissolved in MeOH-acetone (3:1) and stored at −20° C. yielding 7 mg of compound 8 as a yellow powder. Compound 8 was identified as rhein based on comparisons of its physical and spectral data to those reported in the literature (Danielsen and Aksnes, Magn. Reson. Chem. 30: 359–360 (1992)).

Fractions K50 to K55 were combined (98 mg) and subjected to SEPHADEX LH-20 chromatography with MeOH and 125 mL fractions M1 to M5 were collected. Fraction M5 (40 mg) was dissolved in MeOH and left at room temperature whereupon 25 mg of compound 4 was obtained as fine yellow needles.

Fractions K63 to K77 were pooled and subjected to SEPHADEX LH-20 with MeOH and 100 mL fractions 01 to 05). Fraction 03 (30 mg) was applied to ODS preparative HPLC with $CH_3CN$—MeOH—$H_2O$—TFA (50:20:30:0.1) yielding 6 mg of yellow amorphous solid. This material was further purified by ODS preparative HPLC under the same conditions and the resultant fraction reduced in vacuo and placed at −20° C yielding 4 mg of compound 6 as fine yellow needles.

Fractions K94 to K100 were reduced in vacuo to dryness yielding 13 mg of orange amorphous solid. This material was dissolved in a minimal volume of MeOH and left at −20° C. providing 7 mg of compound 3 as orange needles.

The 6 compounds (compounds 1, 2, 3, 4, 6, and 8) were obtained in the yields given in Table 1.

TABLE 1

Yield of the twelve compounds isolated from H. Fulva "Kwanzo" roots.

| Compound | Yield (mg/kg) |
|---|---|
| 1 | 4.8 |
| 2 | 4.8 |
| 3 | 11.1 |
| 4 | 18.0 |
| 6 | 3.8 |
| 8 | 4.7 |

Table 2 shows the yields of the hexane, ethyl acetate, and methanol extracts from 2.0 kg of lyophilized roots and the yield of the compounds in each of the extracts.

TABLE 2

Yield of compounds in extracts from 2.0 kg of lyophilized roots

| | Yield | | | |
|---|---|---|---|---|
| Compound | hexane extract (25 g) | ethyl acetate extract (23 g) | methanol extract (130 g) | Combined Yield |
| 1 + 2 | 19 mg | — | — | 19 mg |
| 3 | — | 15.4 mg | 16.7 mg | 22.1 mg |
| 8 | — | 9.3 mg | — | 9.3 mg |
| 4 | — | 1.0 mg | 34.9 mg | 35.9 mg |
| 6 | — | 3.4 mg | 4.1 mg | 7.5 mg |
| 1a + 2a | NA | NA | NA | NA |

EXAMPLE 2

The physical characteristics of compounds 1 and 2 were determined to be as follows.

$^1H$ NMR spectra were recorded at 500 and 600 MHz on Varian VRX (500 MHz) and Varian INOVA (600 MHz) instruments (Palo Alto, Calif.), respectively. 13C NMR spectra were obtained at 125 MHz on a Varian VRX instrument. NMR spectra of compounds 1 and 2 were obtained in $CDCl_3$. Standard pulse sequences were employed for all 1D ($^1H$, $^{13}C$, DEPT, selective $^1H$ decoupling, and difference NOE) and 2D (DQF-COSY, long-range COSY, NOESY, HMQC, and HMBC) NMR experiments. Mass spectra were acquired at the Michigan State University Mass Spectrometry Facility using a JOEL AX-505H double-focusing mass spectrometer operating at 70 eV for EIMS analysis and a JOEL HX-110 double-focusing mass-spectrometer (Peabody, Mass.) operating in the positive ion mode for FABMS experiments. The UV spectra were recorded in EtOH using a Shimadzu UV-260 recording spectrophotometer (Kyoto, Japan). IR spectra were obtained on a Mattson Galaxy Series FTIR 3000 using WinFIRST software (Thermo Nicolet, Madison, Wis.). Optical rotations were measured with a Perkin-Elmer Polarimeter 341 (Shelton, Conn.). Melting points were determined using a Thomas Model 40 Hot Stage (Philadelphia, Pa.).

The hexane extract was subjected to a series of chromatographic procedures leading to the isolation of 12 mg of fine yellow needles following crystallization from $CHCl_3$-hexane. Initial inspection of the $^1H$ and $^{13}C$ NMR spectra of this product indicated a doubling of most proton and carbon signals that suggested it was perhaps a large dimeric compound composed of more than 31 unique carbon nuclei. However, positive FABMS indicated a major signal at m/z 295 $[M+H]^+$ that suggested the product was a mixture of two structurally related isomers each with a formula of $C_{18}H_{14}O_4$. This was supported by the presence a significant fragment ion at m/z 273 $[M+H-H_2O]^+$. Further evidence was also provided by HMBC experiment that showed two sets of contours representing the $^{2-3}J_{CH}$ connectivities for two compounds each composed of 18 carbon and 14 proton spins. Extensive efforts to separate these two compounds employing Si gel MPLC and TLC, ODS MPLC and preparative HPLC, and crystallization using a variety of solvent systems proved unsuccessful. Further attempts were made to separate the acetylated products (1a and 2a) from one another, but this method also failed. Therefore, the structure elucidation and full $^1H$ and $^{13}C$ NMR assignments of compounds 1 and 2 were performed on the inseparable 1:1 mixture of these two constitutional isomers.

Compounds 1 and 2 were determined to each be composed of substituted 1-hydroxyanthraquinone moieties. Evidence for this came from a combination of HRFABMS with m/z 295.0971 [M+H]$^+$ (calculated 295.0970) and spectroscopic studies. The IR spectrum of compound 1 and 2 exhibited a number of diagnostic absorption bands at 3438 (broad, O—H stretch), 1670 (C=O stretch, non-chelated), and 1633 cm$^{-1}$ (C=O stretch, chelated). The UV spectrum showed $\lambda_{max}$=403 nm suggesting the presence of a single peri-hydroxyl functionality (Schripsema et al., Phytochem. 51: 55–60 (1999)). This was supported by the $^1$H NMR spectrum that revealed two sharp singlets at $\delta_H$ 12.90 and 12.95 that were both eliminated upon D$_2$O exchange. Further evidence for the presence of a single hydroxyl functionality in compounds 1 and 2 came from their acetylation products 1a and 2a that both exhibited the same molecular ion at m/z 337.1068 [M+H]$^+$ (calculated for C$_{20}$H$_{17}$O$_5$, 337.1076) representing the addition of an acetyl moiety. The $^1$H NMR spectrum of 1a and 2a no longer displayed any down field peaks between $\delta_H$ 12 and 13 while the $^{13}$C NMR spectrum exhibited new signals at $\delta_C$ 19.6 (—COCH$_3$) and 169.0 (—COCH$_3$).

$^1$H NMR and DEPT experiments revealed the presence of two aromatic ($\delta_C$ 20.2 q×2, 21.9 q, and 22.0 q) and one acetyl ($\delta_C$ 31.9 q×2) methyl groups in both compounds 1 and 2. Data from the HMBC experiment (Table 3) provided evidence for the assignment of these functionalities as shown for compounds 1 and 2. Further support in favor of this conclusion was obtained from long-range COSY and difference NOE experiments FIGS. 2A and 2B. Both compounds 1 and 2 exhibited reciprocal NOE correlations upon irradiation of the methyl protons of C-12 (both $\delta_H$ 2.59) and 1-OH's ($\delta_H$ 12.95 and 12.90, respectively). In addition, NOE enhancements and long-range COSY correlations were noted between the methyl protons of C-13 (both $\delta_H$ 2.37) and the H-4 aromatic singlet (both $\delta_H$ 7.61). Together, these data confirmed the proposed ring B assignments for compounds 1 and 2.

Figure 2A:
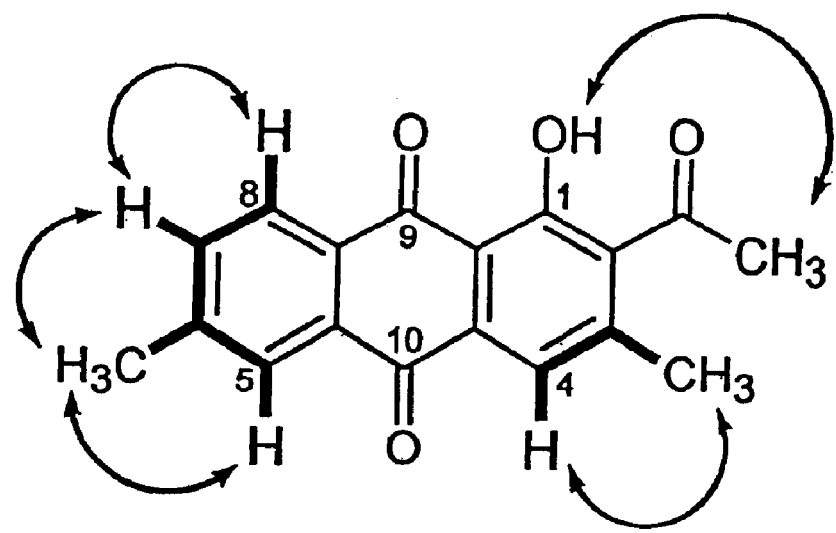
FIG. 2A shows the difference NOE (→) and long-range COSY (-) correlations used to establish the structure of compound 1 (kwanzoquinone A).
Figure 2B:
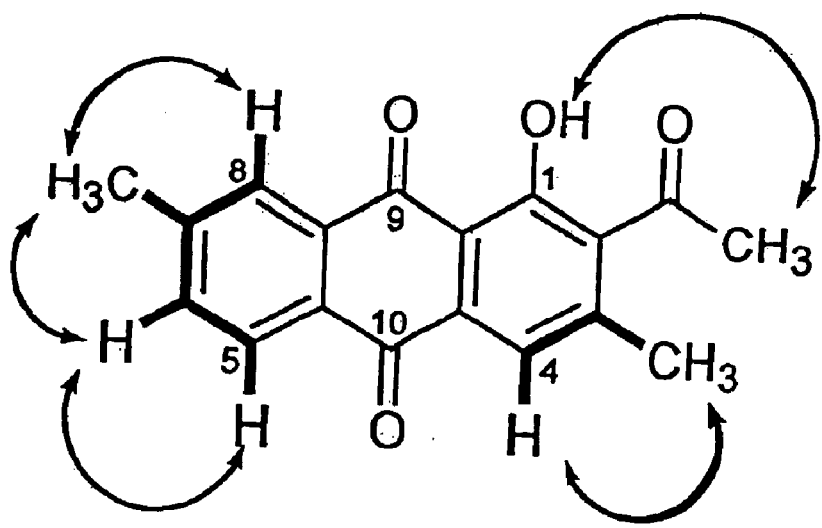
FIG. 2B shows the difference NOE (→) and long-range COSY (-) correlations used to establish the structure of compound 2 (kwanzoquinone B).

Compound 1 exhibited reciprocal NOE enhancements and COSY correlations amongst H-7 ($\delta_H$ 7.58 d, J=7.5 Hz) and H-8 ($\delta_H$ 8.15 d, J=7.5 Hz), as well as, between the methyl protons of C-14 ($\delta_H$ 2.51 s) and protons at positions H-7 and H-5 ($\delta_H$ 8.04 s) (FIG. 2A). These evidence confirmed that the aromatic methyl C-14 ($\delta_H$ 21.9) was attached at position 6 on ring A of compound 1. Compound 2 differed by displaying reciprocal NOE enhancements and long-range COSY correlations between the methyl protons of C-14 ($\delta_H$ 2.51 s) and protons H-6 ($\delta_H$ 7.58 d, J=7.5 Hz) and H-8 ($\delta_H$ 8.05 s) (FIG. 2B). Similar NOE and COSY correlations were noted between H-6 and H-5 ($\delta_H$ 8.13 d, J=7.5 Hz). Therefore, the assignment of the aromatic methyl C-14 ($\delta_C$ 22.0) was confirmed at position 7 on ring A of compound 2. Both compounds 1 and 2 are newly discovered compounds which have been given the name kwanzoquinones A and B, respectively in honor of their biogenic source.

Kwanzoquinones A and B (compounds 1 and 2): yellow needles; melting point 165–167° C.; UV $\lambda_{max}$ (EtOH) 212, 262, 287, 403 nm; IR (KBr) $\nu_{max}$ 3438, 1700, 1696, 1691, 1685, 1670, 1652, 1630, 1595, 1559 cm$^{-1}$; $^1$H NMR $^{13}$C NMR data, see Table 3; HRFABMS m/z 295.0971 [M+H]$^+$ (calculated for C$_{18}$H$_{15}$O$_4$, 295.0970).

TABLE 3

NMR Spectra Data for Kwanzoquinones A (1) and B (2) in CDCL$_3$[a]

| | 1 | | | 2 | | |
|---|---|---|---|---|---|---|
| position | $\delta_h$(J in Hz)[b] | $\delta_C$[c] | HMBC[d] | $\delta_h$(J in Hz)[b] | $\delta_C$[c] | HMBC[d] |
| 1 | | 159.6(s) | 1-OH | | 159.6(s) | 1-OH |
| | | | 1-OH,H-13, | | | 1-OH,H-13, |
| 2 | | 114.4[e](s) | H-4 | | 114.5[e](s) | H-4 |
| 3 | | 144.7[f](s) | H-4,H-13 | | 144.9[f](s) | H-4,H-13 |
| 4 | 7.61(s) | 121.5(d) | H-13 | 7.61(s) | 121.5(d) | H-13 |
| 4a | | 133.1(s) | H-4 | | 133.19(s) | H-4 |
| 5 | 8.04(s) | 127.8(d) | H-14 | 8.13(d,7.5) | 127.7(d) | H-6 |
| 6 | | 146.2(s) | H-8,H-14 | 7.58(d,7.5) | 135.6(d) | H-8,H-14 |
| 7 | 7.58(d,7.5) | 135.1(d) | H-5,H-14 | | 145.6(s) | H-5,H-14 |
| 8 | 8.15(d,7.5) | 127.1(d) | H-7 | 8.05(s) | 127.2(d) | H-14 |
| 8a | | 133.4(s) | H-8 | | 131.2(s) | H-8 |
| 9 | | 188.1(s) | H-8 | | 188.5(s) | H-8 |
| 9a | | 135.7[g](s) | 1-OH,H-4 | | 135.8[g](s) | 1-OH,H-4 |
| 10 | | 182.3(s) | H-4,H-5 | | 181.9(s) | H-4,H-5 |
| 10a | | 130.9(s) | H-5 | | 133.0(s) | H-5 |
| 11 | | 203.0(s) | H-12 | | 203.0(s) | H-12 |
| 12 | 2.59(s) | 31.9(q) | | 2.59(s) | 31.9(q) | |
| 13 | 2.37(s) | 20.2(q) | H-4 | 2.37(s) | 20.2(q) | H-4 |
| 14 | 2.51(s) | 21.9[h](q) | H-5,H-7 | 2.51(s) | 22.0[h](q) | H-6,H-8 |
| 1-OH | 12.95(s) | | | 12.90(s) | | |

[a]All spectra were recorded using 12 mg of a 1:1 mixture of compounds 1 and 2 dissolved in 1 mL of CDCL$_3$ with a 5 mm probe at 25° C.
[b]Recorded at 500 MHz.
[c]Recorded at 125 MHz. Multiplicities were determined by DEPT experiment.
[d]HMBC data were recorded using a $^n$J$_{CH}$ = 8 Hz and are expressed as protons exhibiting $^{2-3}$J$_{CH}$ couplings to the carbons as indicated.
[e-h]Assignments may be interchanged.

EXAMPLE 3

The physical characteristics for compound 3 were determined as in Example 2 except that all NMR spectra were recorded in DMSO-d$_6$ (Cambridge Isotope Laboratories, Inc., Andover, Mass.). The characteristics are as follows.

The MeOH extract was subjected to repeated ODS and SEPHADEX LH-20 gel column chromatography yielding compounds 3, 4, 6, and 8. Following purification, compound 3 was obtained from MeOH as orange needles. HREIMS (m/z 270.0532 [M]$^+$ (calculated for $C_{15}H_{10}O_5$, 270.0528)) and spectral evidence (IR, UV, ID and 2D NMR) confirmed that compound 3 (1,2,8-trihydroxy 3-methylanthraquinone) had been previously isolated from *Myrsine africana* L. (Myrsinaceae) and was given the trivial name 2-hydroxychrysophanol (Li and McLaughlin, J. Nat. Prod. 52: 660–662 (1989); Midiwo and Arot, Int. J. BioChemiPhysics 2: 115–116 (1993)). Previous studies had only given partial $^1$H and no $^{13}$C NMR assignments for this compound; therefore, we undertook a thorough NMR investigation of compound 3 in order to confirm its proposed structure. This is the first report of compound 3 from daylilies and the first report of its complete $^{13}$C NMR spectral date (Table 4).

2-Hydroxychrysophanol (compound 3): orange needles; melting point 239–240° C.; UV $\lambda_{max}$ (EtOH) (log$\epsilon$) 208 (4.19), 235 (4.05), 258 (4.11), 426 (3.73) nm; IR (KBr) $v_{max}$ 3408, 1653, 1620, 1560, 1473, 1456, 1434, 1310, 1271, 1190, 1023 cm$^{-1}$; $^1$H NMR (DMSO-d$_6$) $\delta_H$ 12.04 (1H, brs, 1-OH), 11.90 (1H, s, 8-OH), 10.34 (1H, brs, 2-OH), 7.76 (1H, dd, 8.0, 7.5, H-6), 7.66 (1H, dd, 7.5, 1.0, H-5), 7.55 (1H, s, H-4), 7.31 (1H, dd, 8.0, 1.0, H-7), 2.26 (1H, s, 3-CH$_3$; $^{13}$C NMR, see Table 4; EIMS m/z 270 [M]$^+$ (100), 253(2), 242(8), 213(4), 196(3), 185(2), 168(5), 139(11); HREIMS m/z 270.0532 [M]$^+$ (calculated for $C_{15}H_{10}O_5$, 270.0528) (for literature values refer to Li and McLaughlin, ibid.; Midiwo and Arot, ibid.).

TABLE 4

$^{13}$C NMR Assignments for Compounds 3 to 7[a]

| position | 3 | 4 | 6 |
|---|---|---|---|
| 1 | 194.4s | 153.9s | 149.1s |
| 2 | 150.2s | 147.7s | 148.4s |
| 3 | 132.3s | 141.4s | 136.7s |
| 4 | 122.8d | 121.5d | 119.0d |
| 4a | 123.1s | 128.02 | 123.3s |
| 5 | 119.0d | 119.0d | 119.1d |
| 6 | 137.3d | 137.1d | 137.4d |
| 7 | 123.7d | 124.1d | 123.7d |
| 8 | 161.2s | 161.2s | 161.3s |
| 8a | 115.9s | 115.9s | 116.0s |
| 9 | 192.2s | 191.5s | 192.3s |
| 9a | 114.3s | 115.2s | 114.6s |
| 10 | 180.1s | 180.8s | 180.2s |
| 10a | 133.7s | 133.2s | 133.8s |
| 11 | 16.4q | 17.2q | 57.8t |
| 12 | | | |
| 1' | | 102.9d | |
| 2' | | 74.2d | |
| 3' | | 76.3d | |
| 4' | | 69.7d | |
| 5' | | 77.3d | |
| 6' | | 60.8t | |
| 1" | | | |
| 2" | | | |
| 3" | | | |

[a]Data recorded in DMSO-d$_6$ at 125 MHz at 25° C. Multiplicities were determined by DEPT experiment and confirmed by analysis of HMQC spectra.

EXAMPLE 4

The physical characteristics for compound 4 were determined as in Example 3. The characteristics are as follows.

The MeOH extract was subjected to repeated ODS and SEPHADEX LH-20 gel column chromatography yielding compounds 4. Compound 4 was obtained as yellow needles and exhibited many spectral characteristics similar to 3. The IR spectrum of 4 revealed absorption bands at 3455 (broad, O—H stretch), 1671 (C=O stretch, non-chelated), and 1624 cm$^{-1}$ (C=O stretch, chelated). The UV spectrum presented a $\lambda_{max}$=429 nm that was in accord with the presence of two peri-hydroxyl functionalities (Schripsema ibid.; Brauers et al., J. Nat. prod. 63: 739–745 (2000); Li et al., J. Nat. Prod. 63: 653–656 (2000)). In addition, the $^1$H NMR spectrum showed two down field peaks ($\delta_H$ 12.00 s and 12.04 brs) that were exchangeable with D$_2$O. Together this evidence supported the presence of a 1,8-dihydroxyanthraquinone chromaphore for compound 4.

FABMS gave m/z 433 [M+H]$^+$ that represented a molecular composition of $C_{21}H_{21}O_{10}$. $^1$H NMR provided important evidence for the substitution pattern of rings B and A in compound 4. Three protons representing an ABC spin system at $\delta_H$ 7.70 (dd, J=1.0, 7.5 Hz), 7.79 (dd, J=7.5, 8.0 Hz), and 7.36 (dd, J=1.0, 8.0 Hz) were identified as occupy contiguous positions attached to C-5, C-6, and C-7, respectively on ring A of compound 4. $^{13}$C NMR and DEPT experiments (Table 4) provided further evidence for the identity of the substituents attached to ring B of compound 4 with one methine ($\delta_C$ 121.5), one C-linked ($\delta_C$ 141.4) methyl ($\delta_C$ 17.2), and two quaternary carbon ($\delta_C$ 147.7 and 153.9) linked with a hetero-atom. These carbons were assigned positions in ring B of compound 4 based on their respective chemical shifts and the results from HMBC and HMQC experiments. Five additional methine ($\delta_C$ 69.7, 74.2, 76.3, 77.3, and 102.9) and one methylene ($\delta_C$ 60.8) spins were observed that exhibited chemical shift values that coincided with those for a glucopyranose moiety. The glucopyranose was assigned a $\beta$-configuration based on the coupling of H-1'($\delta_H$5.07, d, J=7.5 Hz). The complete structure of compound 4 was confirmed based on HMBC experiment. Compound 4 is a newly discovered anthraquinone glycoside which has been given the name kwanzoquinone C.

Kwanzoquinone C (compound 4): fine yellow needles; melting point 233–234° C.; [$\alpha$]$^{20}_D$-46° (c 0.031, EtOH); UV $\lambda_{max}$ (EtOH) (log$\epsilon$) 206(4.20), 227(4.23), 260(4.17), 429 (3.78) nm; IR (KBr) $v_{max}$ 3422, 1671, 1624, 1559, 1473, 1382, 1373, 1293, 1263, 1067 cm$^{-1}$; $^1$H NMR (DMSO-d$_6$) $\delta_H$ 12.04 (1H, brs, 8-OH), 12.00 (1H, s, 1-OH), 7.79 (1H, dd, J=7.5, 8.0 Hz, H-6), 7.70 (1H, dd, J=1.0, 7.5 Hz, H-5), 7.61 (1H, s, H-4), 7.36 (1H, dd, J=1.0, 8.0 Hz), 5.07 (1H, d, J=7.5 Hz, H-1'), 3.60 (1H, ddd, J=2.0, 5.5, 12.0 Hz, H-6a'), 342 (1H, ddd, J=6.0, 11.5, 11.5 Hz, H-6b'), 3.31 (1H, m, H-2'), 2.35 (1H, m, H-3'), 3.16 (1H, m, H-4'), 3.13 (1H, m, H-5'), 2.42 (3H, s, H-11); $^{13}$C NMR data, see Table 4; HRFABMS m/z 433.1139 [M+H]$^+$ (calculated for $C_{21}H_{21}O_{10}$, 433.1135).

EXAMPLE 5

The physical characteristics for compound 6 were determined as in Example 3. The characteristics are as follows.

The MeOH extract was subjected to repeated ODS and SEPHADEX LH-20 gel column chromatography yielding compound 6. EIMS analysis of compound 6 gave a molecular ion of m/z 286 [M]$^+$ indicating a molecular formula of $C_{15}H_{10}O_6$. The UV ($\lambda$=426 nm) and IR (absorption bands at 3469 (broad, O—H stretch), 1667 (C=O stretch, non-chelated), and 1620 cm$^{-1}$ (C=O stretch, chelated)) spectra suggested a 1,8-dihydroxyanthraquinone chromaphore for compound 6.

The $^1$H NMR spectrum provided evidence for four exchangeable protons at $\delta$ 12.06, 11.92, 10.47, and 5.40 representing three aromatic and one aliphatic hydroxyl functionalities. An ABC spin system was observed with protons at $\delta_H$ 7.70 (dd, J=0.5, 7.8 Hz), 7.78 (overlapping dd, J=7.8, 7.8 Hz), and 7.33 (dd, J=0.5, 7.8 Hz) occupy contiguous positions attached to C-5, C-6, and C-7, respectively on ring A of compound 6.

Figure 3:
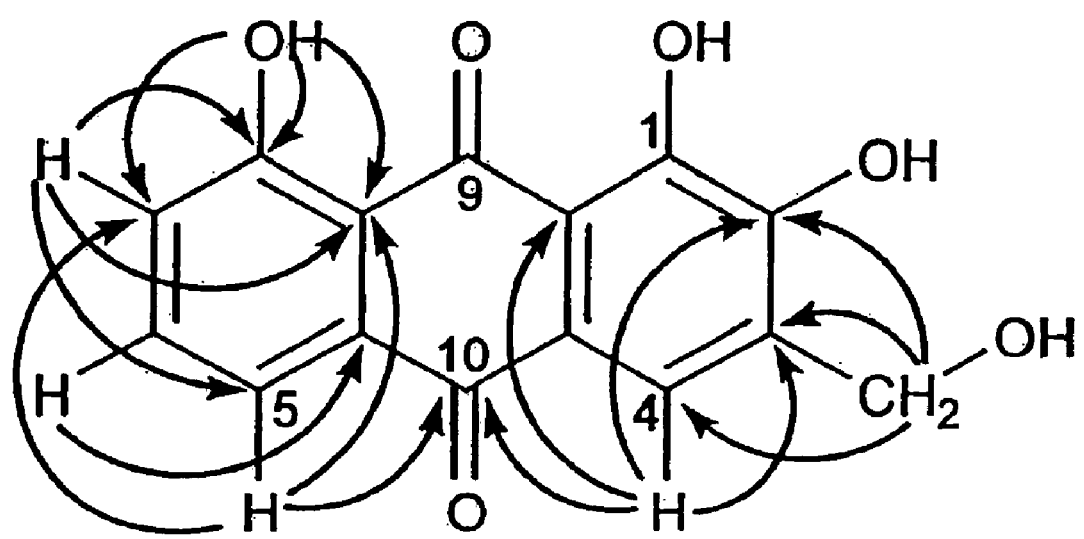
FIG. 3 shows selected HMBC correlations used to determine the structure of compound 6 (kwanzoquinone E).

$^1$H and $^{13}$C NMR and DEPT experiments of compound 6 (Table 4) gave evidence that ring A possessed quaternary carbons with ortho-hydroxyl functionalities (δ 149.1 s and 148.4 s), a hydroxy-methylene moiety $\delta_H$ 4.59 s, 2H and $\delta_C$ 57.8 t) attached to a quaternary carbon ($\delta_C$ 136.7), and a methine ($\delta_C$ 119.0). An HMBC experiment was used to make full assignments of these proton and carbon spins as shown for compound 6 (FIG. 3). Compound 6 is a newly discovered which has been named kwanzoquinone E.

Kwanzoquinone E (compound 6): fine yellow needles; melting point 196–197° C.; UV $\lambda_{max}$ (EtOH) (logε) 209 (4.32), 235(4.10), 258(4.27), 354(3.72), 426(3.76) nm; IR (KBr) $v_{max}$ 3469, 1652, 1619, 1559, 1473, 1458, 1382, 1321, 1273, 1092 cm$^{-1}$; $^1$H NMR (DMSO-d$_6$) $\delta_H$ 12.06 (1H, brs, 1-OH), 11.92 (1H, s, 8-OH), 10.47 (1H, brs, 2-OH), 7.87 (1H, d, J=0.5 Hz, H-4), 7.78 (1H, dd, J=7.8, 7.8 Hz, H-6), 7.70 (1H, dd, J=0.5, 7.8 Hz, H-5), 7.33 (1H, dd, J=0.5, 7.8 Hz, H-7), 5.40 (1H, brs, 11-OH), 4.59 (2H, s, H-11); $^{13}$C NMR data, see Table 4; EIMS m/z 286 [M]$^+$ (62), 268(89), 240(56), 212(100), 184(50), 155(14), 128(19), 120(19); HREIMS m/z 286.0479 [M]$^+$ (calculated for $C_{15}H_{10}O_5$, 286.0477).

EXAMPLE 6

The MeOH extract was subjected to repeated ODS and SEPHADEX LH-20 gel column chromatography yielding compound 8. Compound 8 was obtained as an amorphous yellow powder and its spectral data were found to match those reported for the known anthraquinone rhein (Danielsen and Aksnes, Magn. Reson. Chem. 30: 359–360 (1992)).

EXAMPLE 7

This example demonstrates that several of compounds 1, 2, 3, 4, 6, and 8, including 1a and 2a, have anti-cancer activity. This was demonstrated by a cancer cell growth inhibition assay was performed as follows.

The compounds were tested for their activity against breast, central nervous system (CNS), colon, and lung human tumor cell lines. The breast (MCF-7), CNS(SF-268), and lung (NCI-H460) cultures were purchased from the National Cancer Institute (Bethesda, Md.) while the colon culture (HCT-116) was purchased from the American Type Culture Collection (Arlington, Va.). All cell lines were maintained in a humidified chamber at 37° C. with 5% CO$_2$ in RPMI-1640 medium supplemented with 10% fetal bovine serum, penicillin (1 unit/100 mL), and streptomycin (1 μg/100 mL). All cell lines were sub-cultured according to their individual growth profiles in order to ensure exponential growth throughout the experiments. Breast (10,000 cells/well), CNS (15,000 cells/well), colon (7,500 cells/well), and lung (7,500 cells/well) cancer cells were aliquoted (100 μL) into 96-well plates and allowed to grow for 24 hours before the addition of the test compounds to the media. The compounds were dissolved in DMSO and diluted in sterile media as necessary to obtain the appropriate concentration. The test compounds were added to the sample wells in 100 μL aliquots so that the final concentration of DMSO did not exceed 0.25%. Test compounds, standards, and DMSO control were incubated for 48 hours, after which the assay was terminated via the addition of cold trichloroacetic acid. The plates were incubated for one hour at 4° C., washed with deionized water (five times), and air-dried. A 100 μL aliquot of 0.4% sulforhodamine B stain in 1% acetic acid was added to each well and the plates were incubated for 30 minutes at room temperature. Following incubation, the wells were rinsed with 1% acetic acid (five times) and the bound stain was dissolved in 100 μL of 10 mM TRIZMA base. The plates were shaken for five minutes on a gyrorotary shaker after which the absorbance of each well was recorded with an automated microplate reader (model EL800, Bio-Tek Instruments, Inc., Winooski, Vt.) at 515 nm. Three independent experiments were performed in triplicate using at least five drug concentrations inclusive of the 50% growth inhibitory concentration. Results are expressed as the concentration of compound required to inhibit cellular growth 50% (GI$_{50}$) ±SE.

It had been previously reported that crude Hemerocallis extracts inhibited fibroblast proliferation and induced cancer cells to undergo differentiation; however, the active constituents have never been identified. Here, for the first time, several compounds obtained from H. fulva roots clearly exhibit growth inhibitory effects against human breast, CNS, colon, and lung cancer cell lines. The GI$_{50}$ concentrations of these compounds are presented in Table 6. The mixtures of compounds 1 and 2, as well as, 1a and 2a exhibited strong growth inhibitory effects against breast cancer cells with GI$_{50}$ values of 2.6±0.6 and 1.8±0.2 mg/mL, respectively. In contrast, the GI$_{50}$ concentration of these compounds was approximately three to six times higher against the other three cell lines (Table 5).

TABLE 5

Growth inhibitory effects of compounds 1, 1a, 2, 2a, 3, 4, 6, and 8 against four human cancer cell lines

| compound | cell line (GI$_{50}$, μg/mL ± SE) | | | |
|---|---|---|---|---|
| | MCF-7 (breast) | SF-268 (CNS) | HCT-116 (colon) | NCI-H460 (lung) |
| 1 and 2 | 2.6 ± 0.6 | 14.7 ± 2.5 | 13.5 ± 0.9 | 10.3 ± 1.2 |
| 1a and 2a | 1.8 ± 0.2 | 5.3 ± 0.8 | 10.5 ± 0.7 | 8.5 ± 0.6 |
| 3 | 6.5 ± 1.2 | 2.4 ± 1.8 | 6.3 ± 0.8 | 6.3 ± 0.8 |
| 4 | 6.7 ± 0.4 | 6.1 ± 1.0 | 7.4 ± 0.6 | 3.8 ± 0.3 |
| 6 | 2.8 ± 0.3 | 3.8 ± 0.7 | 5.0 ± 0.3 | 7.3 ± 0.7 |
| 8 | 17.2 ± 0.8 | 16.3 ± 1.8 | 21.1 ± 1.8 | 15.4 ± 1.7 |
| adriamycin[a] | 1.7 ± 0.2 | 1.9 ± 0.7 | 2.1 ± 0.6 | 1.7 ± 0.4 |

[a]Values for adriamycin are expressed in μM.

Compounds 3, 4, and 6 exhibited consistent activity against all four cancer cell lines (Table 5). The in vitro cytotoxicity of compound 3 against three tumor cell lines described in Li and McLaughlin, J. Nat. Prod. 52: 660–662 (1989) including lung (A-549, ED$_{50}$ 3.1 μg/mL), nasal (KBMRI, ED$_{50}$ 5.7 μg/1 mL), and colon (HT-29, ED$_{50}$ 2.8 μg/mL) had been previously described. The results for compound 3 are consistent with the previously reported findings. Compounds 4 and 6 are both new compounds that represent 2-O-glucopyranose conjugated and 3-hydroxymethyl derivatives, respectively, of compound 3. Both of these compounds were found to possess cancer cell growth inhibitory properties against all cell lines tested at concentrations similar to that of compound 3. Compound 8 exhibited moderate activity against all four cancer cell lines.

In light of the growth inhibitory activity exhibited by these compounds against a number of cancer cell lines and the current cancer chemotherapeutic application of other anthraquinone derivatives, compounds 1, 1a, 2, 2a, 3, 4, 6, and 8 have useful clinical applications for the treatment of particular cancers.

EXAMPLE 14

In this example, compounds 1, 1a, 2, 2a, 3, 4, 6, and 8 were tested for cell toxicity using an 3-[4,5-dimethylthiazol- 2-yl]-2,5-diphenyltetrazolium bromide (MTT) cell viability assay. The assay monitors the conversion of MTT to the dye, formazan, by viable cells. The formazan crystals form a precipitate which is dissolved in DMSO and analyzed by spectroscopy. MTT is not converted to formazan by dead cells. Therefore, the amount of dye detected is inversely related to the toxicity of the compound being tested.

The cancer cells used were HCT 116 (colon carcinoma, human, batch # F-11276), SF-268 (CNS, glioblastoma, human, 0503138), NCI-H460 (lung, large cell carcinoma, human, 503473), and MCF-7 (breast, mammary adenocarcinoma, human, 0501975) were procured from NCI, NIH.

The cells were grown in RPMI 1640 media supplemented with 10% fetal bovine serum and maintained at 37° C. in a humidified atmosphere of 5% $CO_2$. Cells were seeded in 96 well plates at a density of 2000 cells per well. Test samples, dissolved in 0.5% DMSO in RPMI 1640 media at the desired concentration, were added to the 96-well plate containing cancer cells which had been incubated for 24 hours. After incubating for 48 hours at 37° C., 25 μL of MTT solution (5 mg/mL in PBS solution) was added into each well of 96-well plate. The plates were then wrapped in aluminum foil and incubated at 37° C. for 3 hours. The media containing MTT and dead cells were removed. To each well, 200 μL of DMSO was added immediately, shaken for 5 min, and optical density of each well was recorded at 570 nm using Universal Microplate Reader.

Each concentration was tested in triplicate and the experiment was repeated three times. Adriamycin was tested as positive control and 0.5% DMSO in RPMI 1640 media was tested as solvent control. The concentration of the compounds tested in the MTT viability assay based on their $GI_{50}$ (μg/mL) values are shown in Table 6.

TABLE 6

Concentration of Compounds Tested Based on $GI_{50}$ Values (μg/mL)

| Sample (compound) | HCT-116 (Colon Cancer) | SF-268 (CNS Cancer) | NCI H-460 (Lung Cancer) | MCF-7 (Breast Cancer) |
|---|---|---|---|---|
| A (1 and 2) | 15.0 | 15.0 | 11.3 | 2.8 |
| B (3) | 7.5 | 2.8 | 7.5 | 7.5 |
| C (8) | 22.5 | 18.8 | 15.0 | 22.5 |
| D (4) | 7.5 | 7.5 | 3.8 | 7.5 |
| F (6) | 5.6 | 2.8 | 7.5 | 2.8 |
| G (1a and 2a) | 11.3 | 5.6 | 11.3 | 1.9 |
| Adriamycin | 0.091 | 0.091 | 0.091 | 0.091 |

The average optical densities of three wells for each sample tested and of DMSO control were calculated. The average optical densities of samples and of DMSO control from the replicates were then calculated. The percentage of average value of optical density between test sample and DMSO control represents the percentage viability of cells exposed to anthraquinones at their $GI_{50}$ concentration (FIGS. 6, 7, 8, and 9).

Figure 4:
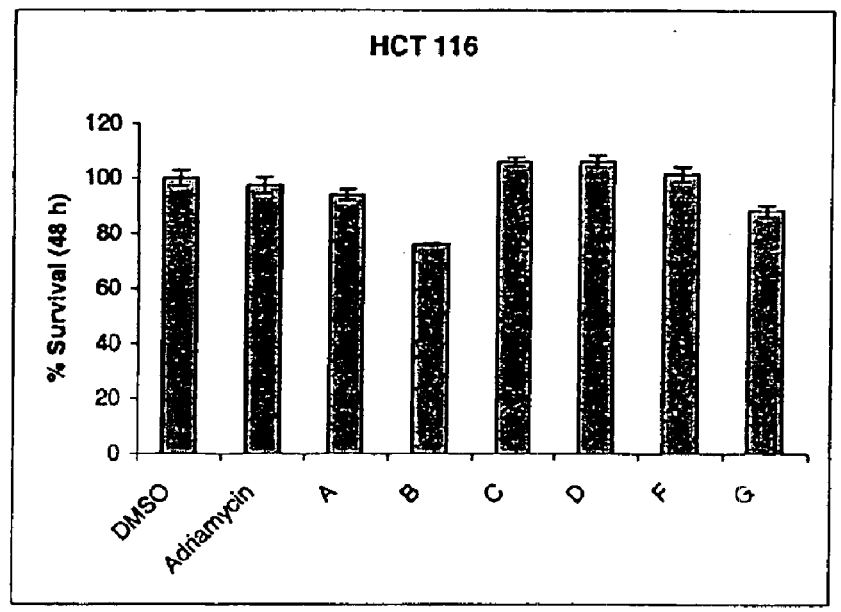
FIG. 4 shows the results of an MTT assay at $GI_{50}$ concentration on the toxicity of compounds 1 and 2 (A), 3 (B), 8 (C), 4 (C), 6 (D), and 1a and 2a (G) compared to adriamycin on HCT 116 human colon carcinoma cells.
Figure 5:
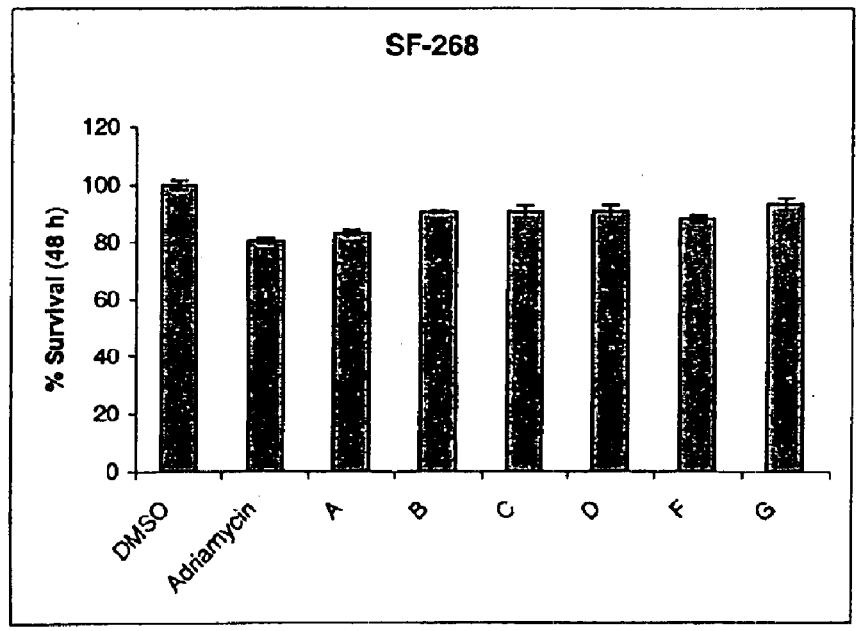
FIG. 5 shows the results of an MTT assay at $GI_{50}$ concentration on the toxicity of compounds 1 and 2 (A), 3 (B), 8 (C), 4 (C), 6 (D), and 1a and 2a (G) compared to adriamycin on SF-268 human CNS glioblastoma cells.
Figure 6:
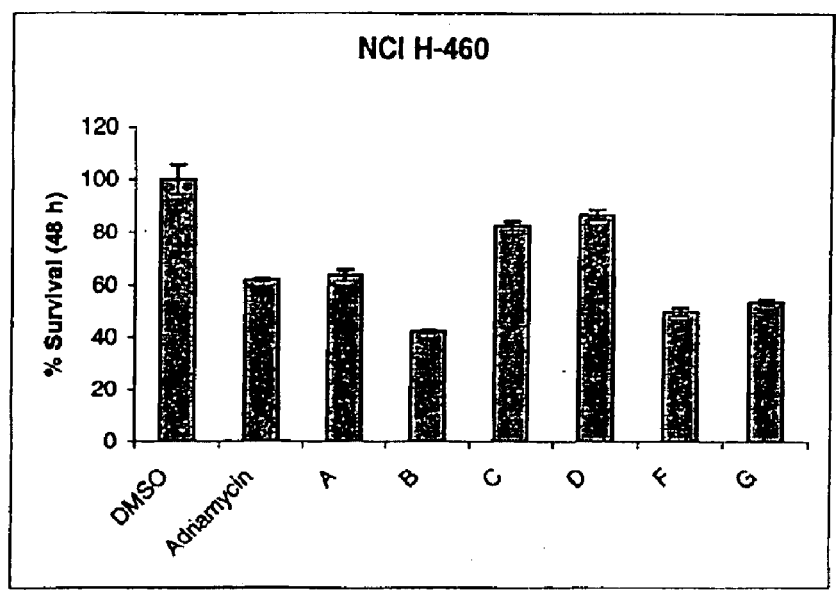
FIG. 6 shows the results of an MTT assay at $GI_{50}$ concentration on the toxicity of compounds 1 and 2 (A), 3 (B), 8 (C), 4 (C), 6 (D), and 1a and 2a (G) compared to adriamycin on NCI-H460 human large cell carcinoma cells.
Figure 7:
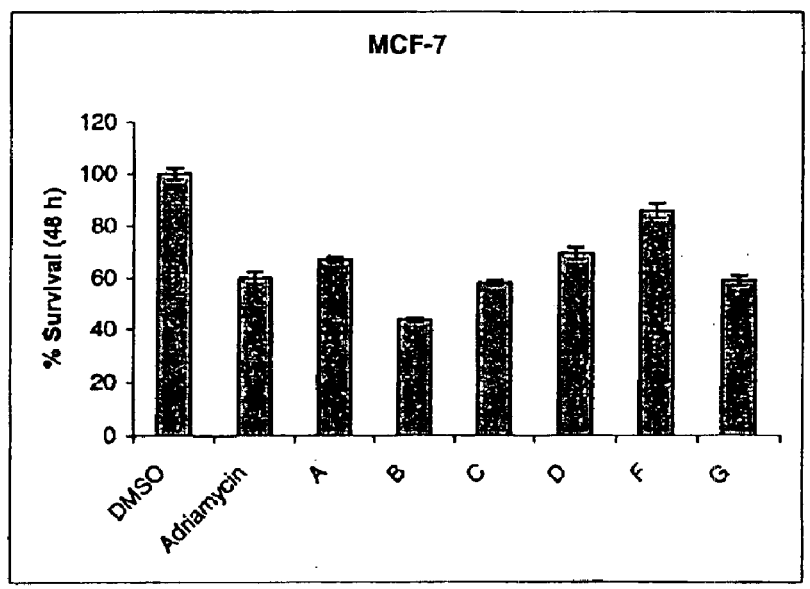
FIG. 7 shows the results of an MTT assay at $GI_{50}$ concentration on the toxicity of compounds 1 and 2 (A), 3 (B), 8 (C), 4 (C), 6 (D), and 1a and 2a (G) compared to adriamycin on MCF-7 human mammary adenocarcinoma cells.

The results show that compounds 3 (B) and a mixture of compounds 1a and 2a (G) demonstrated higher toxicity than the rest of the anthraquinones in HCT 116 (Colon cancer) assay (FIG. 4). Similarly, a mixture of compounds 1 and 2 (A) or compound 3 (B) showed higher toxicity than compound 8 (C), compound 4 (D), compound 6 (F), and a mixture of compounds 1a and 2a G in SF-268 (CNS cancer) assay (FIG. 5); compounds 8 and 4 (C and D, respectively) were the lest toxic in NCI H460 (Lung cancer) assay (FIG. 6), and all sample except compound 6 (F) showed considerable toxicity in MCF-7 (Breast cancer) assay (FIG. 7).

While the present invention is described herein with reference to illustrated embodiments, it should be understood that the invention is not limited hereto. Those having ordinary skill in the art and access to the teachings herein will recognize additional modifications and embodiments within the scope thereof. Therefore, the present invention is limited only by the claims attached herein.

We claim:

1. A method for inhibiting growth of cells of a cancer or a tumor, which comprises:

exposing the cells to one or more anthraquinones with the chemical formula:

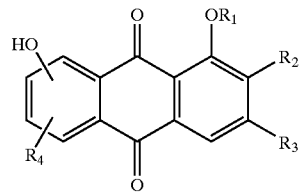

wherein $R_1$ is selected from the group consisting of hydrogen, and acetyl; $R_2$ is selected from the group consisting of methyl, acetyl hydroxyl, hydroxymethyl, and carbohydrate groups; $R_3$ is selected from the group consisting of methyl, hydroxymethyl, carbohydrate, each of these $R_3$ containing 1 to 12 carbon atoms, and hydroxyl groups, and $R_4$ is selected from the group consisting of hydrogen and methyl, but not an anthraquinone wherein $R_1$ is hydrogen, $R_2$ is hydroxyl, $R_3$ is methyl, $R_4$ is hydrogen, in an amount sufficient to inhibit growth of the cells.

2. The method of claim 1 wherein the one or more anthraquinones are selected from the group consisting of 1-hydroxy-2-acetyl-3,6-methyl anthraquinone, 2-acetyl-3,6-methyl anthraquinone monoacetate, 1-hydroxy-2-acetyl-3,7-methyl anthraquinone, 2-acetyl-3,7-methyl anthraquinone monoacetate, 1,8-dihydroxy-2-O-β-D-glucopyranoside anthraquinone, and 1,2,8-trihydroxy-3-hydroxymethyl anthraquinone.

3. The method of claim 1 or 2 which further comprises at least one compound selected from the group consisting of 1,2,8-trihydroxy-3-methyl anthraquinone, 1,8-dihydroxy-3-carboxy anthraquinone, and adriamycin with the anthraquinones for exposing the cells to inhibit growth of the cells.

4. The method of claim 1 wherein the cells are selected from the group consisting of breast cancer, central nervous system cancer, lung cancer, and colorectal cancer.

5. The method claim 1 wherein the inhibiting is either in vivo or in vitro.

6. The method of claim 1 wherein the one or more anthraquinones are at a dosage of about 0.1 to 4,000 micrograms per milliliter or gram of a medium for exposing the cells.

7. A method for inhibiting growth of a cancer or tumor in a patient with the cancer or tumor comprising:

(a) providing a composition containing an inhibitory amount of one or more anthraquinones with the chemical formula:

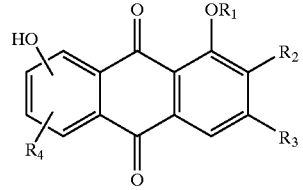

wherein R$_1$ is selected from the group consisting of hydrogen and acetyl; R$_2$ is selected from the group consisting of methyl, acetyl, hydroxyl, hydroxymethyl, and carbohydrate groups; R$_3$ is selected from the group consisting of methyl, hydroxymethyl, and carbohydrate groups, each of these R$_3$ containing 1 to 12 carbon atoms, and hydroxyl groups and R$_4$ is selected from the group consisting of hydrogen and methyl, but not an anthraquinone wherein R$_1$ is hydrogen, R$_2$ is hydroxyl, R$_3$ is methyl and R$_4$ is hydrogen, in a pharmaceutically acceptable carrier; and (b) administering the composition to the patient in an amount sufficient to inhibit growth of the cancer or tumor.

8. The method of claim 7 wherein the one or more anthraquinones are selected from the group consisting of 1-hydroxy-2-acetyl-3,6-methyl anthraquinone, 2-acetyl-3,6-methyl anthraquinone monoacetate, 1-hydroxy-2-acetyl-3,7-methyl anthraquinone, 2-acetyl-3,7-methyl anthraquinone monoacetate, 1,8-dihydroxy-2-O-β-D-glucopyranoside anthraquinone, and 1,2,8-trihydroxy-3-hydroxymethyl anthraquinone.

9. The method of claim 7 or 8 wherein the composition further includes at least one compound selected from the group consisting of 1,2,8-trihydroxy-3-methyl anthraquinone, 1,8-dihydroxy-3-carboxy anthraquinone, and adriamycin.

10. The method of claim 8 wherein the cancer or tumor is selected from the group consisting of breast cancer, central nervous system cancer, lung cancer, and colorectal cancer.

11. The method of claim 8 wherein the anthraquinone is at a dosage of about 0.1 to 4,000 micrograms per milliliter or gram of the composition for exposing the cells.

12. The method of claim 8 wherein the composition is administered to the patient by a method selected from the group consisting of oral, subcutaneous, intraperitoneal, topical, intranasal, intravenous, or rectal.

13. A composition for inhibiting growth of cells of a cancer or a tumor which comprises:

(a) one or more anthraquinones with the chemical formula:

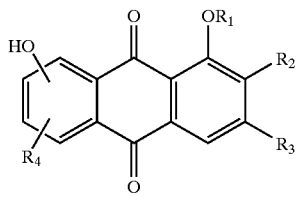

wherein R$_1$ is selected from the group consisting of hydrogen and carboxy; R$_2$ is selected from the group consisting of methyl, acetoxy, hydroxyl, hydroxymethyl, and carbohydrate groups; and R$_3$ is selected from the group consisting of methyl, hydroxymethyl, acid and carbohydrate groups, each of these R$_3$ containing 1 to 12 carbon atoms, and a hydroxyl group, and R$_4$ is selected from the group consisting of hydrogen and methyl, but not an anthraquinone wherein R$_1$ is hydrogen, R$_2$ is hydroxyl, R$_3$ is methyl and R$_4$ is hydrogen; and (b) a pharmaceutically acceptable carrier, wherein the composition contains between about 0.1 and 4,000 micrograms of the anthraquinone per milliliter or gram of the carrier.

14. The composition of claim 13 wherein the one or more anthraquinones are selected from the group consisting of 1-hydroxy-2-acetyl-3,6-methyl anthraquinone, 2-acetyl-3,6-methyl anthraquinone monoacetate, 1-hydroxy-2-acetyl-3,7-methyl anthraquinone, 2-acetyl-3,7-methyl anthraquinone monoacetate, 1,8-dihydroxy-2-O-β-D-glucopyranoside anthraquinone, and 1,2,8-trihydroxy-3-hydroxymethyl anthraquinone.

15. The composition of claim 13 or 14 which further includes at least one compound selected from the group consisting of 1,2,8-trihydroxy-3-methyl anthraquinone, 1,8-dihydroxy-3-carboxy anthraquinone, and adriamycin.

16. A purified anthraquinone which has the formula:

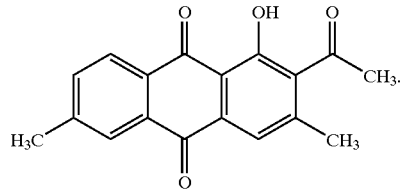

17. A purified anthraquinone which has the formula:

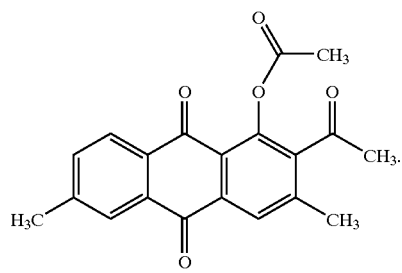

18. A purified anthraquinone which has the formula:

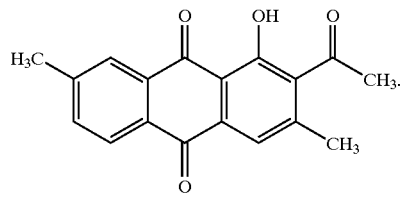

19. A purified anthraquinone which has the formula:

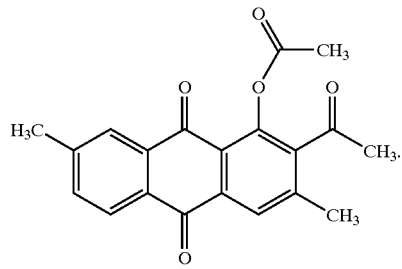

20. An anthraquinone which has the formula:

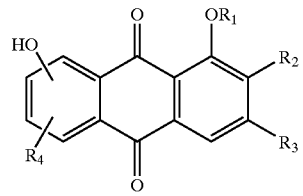

wherein R$_1$ is selected from the group consisting of hydrogen and acetyl; R$_2$ is selected from the group consisting of methyl, acetyl, hydroxy, hydroxymethyl, carboxylic acid, and carbohydrate groups; R$_3$ is selected from the group consisting of hydroxymethyl and carbohydrate groups, each of these R$_3$ containing 1 to 12 carbon atoms; and R$_4$ is selected from the group consisting of hydrogen and methyl.

* * * * *

UNITED STATES PATENT AND TRADEMARK OFFICE
CERTIFICATE OF CORRECTION

PATENT NO.   : 6,875,746 B1
DATED        : April 5, 2005
INVENTOR(S)  : Muraleedharan G. Nair et al.

It is certified that error appears in the above-identified patent and that said Letters Patent is hereby corrected as shown below:

Column 1,
Line 6, after "application" and before "is" "is application" (second occurrence) should be deleted.
Line 46, "in an" after "thereof" should be deleted.

Column 3,
Line 37, "anthroquinone" should be -- anthraquinone --.

Column 4,
Line 18, "anthroquinone" should be -- anthraquinone --.

Column 5,
Line 1, "anthroquinone" should be -- anthraquinone --.

Column 5,
Line 1, "anthroquinone" should be -- anthraquinone --.

Column 6,
Line 35, "anthroquinone" should be -- anthraquinone --.

Column 12,
Line 8, "to is stomach" should be -- to stomach --.
Line 49, "nthraquinones" should be -- anthraquinones --.

Column 22,
Lines 45 and 46, after "McLaughlin J." and before "Nat. Prod." the paragraph indicator should be deleted.
Line 47, "ED50 5.7 g/1 mL" should be -- ED50 5.7 g/ mL --.

UNITED STATES PATENT AND TRADEMARK OFFICE
CERTIFICATE OF CORRECTION

PATENT NO. : 6,875,746 B1
DATED : April 5, 2005
INVENTOR(S) : Muraleedhar G. Nair et al.

It is certified that error appears in the above-identified patent and that said Letters Patent is hereby corrected as shown below:

Column 23,
Line 65, "lest toxic" should be -- least toxic --.

Signed and Sealed this

Nineteenth Day of July, 2005

JON W. DUDAS
*Director of the United States Patent and Trademark Office*